United States Patent [19]

Ost et al.

[11] 4,198,410

[45] Apr. 15, 1980

[54] LIQUID FUNGITOXIC AND ACARICIDAL COMPOSITIONS CONTAINING TRIFORINE

[75] Inventors: Walter Ost, Bingen; Klaus Thomas, Gau-Algesheim, both of Fed. Rep. of Germany

[73] Assignee: Celamerck GmbH & Co. KG, Ingelheim am Rhein, Fed. Rep. of Germany

[21] Appl. No.: 903,576

[22] Filed: May 8, 1978

Related U.S. Application Data

[63] Continuation of Ser. No. 844,594, Oct. 25, 1977, abandoned, which is a continuation of Ser. No. 686,174, May 13, 1976, abandoned.

[30] Foreign Application Priority Data

May 14, 1975 [DE] Fed. Rep. of Germany ....... 2521384

[51] Int. Cl.$^2$ ............................................. A01N 9/22
[52] U.S. Cl. .................................................... 424/250
[58] Field of Search ................................ 424/250, 358

[56] References Cited

U.S. PATENT DOCUMENTS 3,696,106  10/1972  Ost et al. .............................. 424/250

FOREIGN PATENT DOCUMENTS 2128225  12/1972  Fed. Rep. of Germany .

OTHER PUBLICATIONS

Kirk–Othmer Encyc. of Chem. Tech., vol. 19 (1969), pp. 511, 515, 516, 517, 518.

Primary Examiner—V. D. Turner
Attorney, Agent, or Firm—Hammond & Littell, Weissenberger & Muserlian

[57] ABSTRACT

Liquid, water-miscible, fungitoxic and acaricidal emulsion concentrates containing triforine and, as an emulsifier, a member of a certain group of salts of alkylbenzene-sulfonic acids, preferably of n-dodecylbenzenesulfonic acid or tetrapropylenebenzenesulfonic acid; the concentrates exhibit markedly improved stability.

7 Claims, No Drawings

LIQUID FUNGITOXIC AND ACARICIDAL COMPOSITIONS CONTAINING TRIFORINE

This is a continuation of copending application Ser. No. 844,594, filed Oct. 25, 1977, now abandoned, which in turn is a continuation of application Ser. No. 686,174, filed May 13, 1976, now abandoned.

This invention relates to novel liquid compositions containing N,N'-bis-(1-formamido-2,2,2-trichloroethyl)-piperazine (also known by its generic name "triforine") and, as an emulsifier, a member of a certain group of salts of alkylbenzenesulfonic acids.

BACKGROUND OF THE INVENTION

It is known that triforine exhibits very effective fungitoxic and acaricidal properties, and that these properties unfold in a particularly advantageous manner when triforine is incorporated as the active ingredient into certain liquid compositions.

U.S. Pat. No. 3,696,106 and German Offenlegungsschrift No. 2,128,225 disclose triforine, as well as fungitoxic, liquid emulsion concentrates containing triforine as the active ingredient. A particular characteristic of those liquid compositions is that they contain dimethylformamide and N-methyl-pyrrolidone as the solvent medium, and the isopropylamine salt or the triethanolamine salt of dodecylbenzenesulfonic acid as the emulsifier. Such emulsion concentrates form, upon dilution with water, highly effective liquid plant protection compositions, but they have the disadvantage that the active ingredient, triforine, has only a limited stability therein. Especially at higher temperatures, but even at only moderately elevated temperatures of about 20° C., the triforine undergoes a noticeable degradation, so that such liquid emulsion concentrate compositions have a relatively short shelf-life under normal conditions or must be stored under special, cost-increasing conditions.

While it is possible to improve the storage stability of liquid emulsion concentrate compositions containing triforine, such as those above referred to, by using a nonionic emulsifier, this modification introduces other significant disadvantages, such as inadequate solubility of the triforine, weaker biological activity and/or inferior spray properties.

THE INVENTION

We have discovered that a significant improvement in stability of triforine in liquid emulsion concentrate compositions is achieved by using a member of a certain group of salts of alkylbenzenesulfonic acids as the emulsifier. This discovery is particularly surprising inasmuch as we have found that even minor alterations in the structure of the cation of the emulsifier salt produce a considerable improvement of the triforine stability. For instance, the substitution of the *di*isopropylamine salt of dodecylbenzenesulfonic acid for the conventional *mono*isopropylamine salt of dodecylbenzenesulfonic acid as the emulsifier in liquid triforine compositions produces an eight-fold increase in the triforine stability at 22° C. The improved storage stability of triforine-containing liquid compositions according to the present invention is particularly well-defined at temperatures below 30° C.

The alkylbenzenesulfonic acids from which the emulsifier salts according to the present invention are derived are preferably n-dodecylbenzenesulfonic acid (DBS) or tetrapropylenebenzenesulfonic acid. The cation moiety of the emulsifier salts is $Ca^{++}$, $Li^+$, $tert.C_4H_9$—$NH_3^+$ or an ammonium ion in which the salt formation is based on a secondary or tertiary aliphatic amine which meets at least one of the following criteria:

1. Strong basicity ($pK_A$-value $> 10.5$);
2. *Branched* alkyl chain of 3–4 carbon atoms; and
3. No additional functional groups in the alkyl radicals.

Examples of suitable such amines are dimethylamine, diethylamine, di-n-propylamine, diisopropylamine, di-sec.butylamine, trimethylamine, triethylamine, tri-n-propylamine, triisopropylamine and tert.butylamine.

Particularly preferred as emulsifiers in accordance with the present invention are the triethylamine salt or the diisopropylamine salt of n-dodecylbenzenesulfonic acid.

Most of the alkylbenzenesulfonic acid salts used as emulsifiers pursuant to the present invention are known compounds; those which are not specifically described in the literature may be prepared by conventional methods, such as by neutralization of the free acid with the desired base in the molten state or in the presence of a solvent. The solvent may be one of the solvent media used for the preparation of the liquid triforine-containing compositions of the present invention, as indicated below.

The following example illustrates the preparation of a salt of an alkylbenzenesulfonic acid which can be used as an emulsifier in accordance with the present invention.

EXAMPLE 1

Triisopropanolamine salt of n-dodecylbenzenesulfonic acid 573 gm (3 mols) of molten triisopropanolamine were added in small portions to 978 gm (3 mols) of n-dodecylbenzenesulfonic acid at 55° C., while vigorously stirring. Toward the end of the neutralization, the temperature was increased to 85° C. After all of the amine had been added, the mixture was heated for one hour at 90° C. and then cooled to room temperature. The resulting viscous substance solidified into a mass of wax-like consistency upon standing for a few days at room temperature.

The liquid triforine-containing concentration compositions of the present invention advantageously contain from 5 to 45% by weight, based on the total weight, of an alkylbenzenesulfonic acid salt emulsifier, and preferably 15–35% by weight of such salts. The compositions may, in addition, also contain from 0.5 to 10% by weight, based on the total weight, of a non-ionic emulsifier, such as an ethoxylated alkylphenol, provided, however, that the total content of emulsifiers in the concentrate does not exceed 45% by weight, based on the total weight.

Dimethylformamide (DMF), N-methyl-pyrrolidone (NMP), dimethylacetamide (DMAC) or a mixture of any two or more of these may be used as the solvent for the preparation of the liquid triforine-containing concentrate compositions of the present invention. However, DMF or a mixture of DMF and NMP in a volumetric ratio of 9:1 to 4:6 are preferred.

A portion of the above-indicated solvent, but no more than 40% thereof, may be replaced by conventional solvents, such as aromatic hydrocarbons or triethyleneglycol, especially when the concentrate composition contains less than 20% triforine. In addition, the concentrate compositions may contain a dye and up to 5% by weight, based on the total weight, of a conventional foam-suppressor, such as a long-chain, branched alcohol.

The liquid concentrate compositions of the present invention may contain from 3 to 30% by weight, and preferably from 5 to 25% by weight, based on the total weight, of triforine; in addition, they may contain other fungicidal, acaricidal and/or insecticidal compounds, and in such cases the total active ingredient content may exceed 30% by weight, based on the total weight.

The manufacture of liquid triforine-containing compositions intended for use as agricultural and horticultural fungicides and acaricides is particularly difficult, because triforine is very sparsely soluble in most of the solvents which can be used for this purpose. While the solubility of triforine in DMF, NMP and DMAC as well as in mixtures of these solvents is relatively good, it is significantly impaired by the addition of conventional emulsifiers. Therefore, if relative large amounts of these emulsifiers are used to prepare liquid, water-miscible, triforine-containing emulsion concentrates, the active ingredient content thereof is limited to relatively low percentages and, moreover, such concentrates often exhibit unsatisfactory cold stabilities.

Thus, an important advantage of the present invention is that the solubility of triforine in the particular solvents above referred to is not impaired by the use of the particular group of alkylbenzenesulfonic acid salts as emulsifiers pursuant to this invention. This effect is especially well-defined in the case of the triethylamine salt of n-dodecylbenzenesulfonic acid and somewhat less well-defined in the case of the diisopropylamine salt of n-dodecylbenzenesulfonic acid.

The following table illustrates the effects of various amine salts of dodecylbenzenesulfonic acid emulsifiers on the solubility of triforine in DMF and a mixture of DMF and NMP, respectively, where IPA-DBS = Monoisopropylamines salt of dodecylbenzenesulfonic acid,
ODA = Isooctadecyl alcohol,
DIPA-DBS = Diisopropylamine salt of dodecylbenzenesulfonic acid, and
TEA = Triethylamine salt of dodecylbenzenesulfonic acid.

TABLE

| Test No. | Amount of Triforine | Emulsifier | Solvent | Amount of solvent required for preparation of which is saturated at 0° C. |
|---|---|---|---|---|
| 1 | 42 gm | none | DMF/NMP 1:1 | 112 gm |
| 2* | 42 gm | 60 gm IPA-DBS +4 gm ODA | DMF/NMP 1:1 | 121 gm |
| 3 | 42 gm | 60 gm DIPA-DBA +4 gm ODA | DMF/NMP 1:1 | 104 gm |
| 4 | 42 gm | 60 gm TEA-DBS +4 gm ODA | DMF/NMP 1:1 | 94 gm |
| 5 | 42 gm | none | DMF | 159 gm |
| 6* | 42 gm | 60 gm IPA-DBS +4 gm ODA | " | 157 gm |
| 7 | 42 gm | 60 gm DIPA-DBS +4 gm ODA | " | 135 gm |
| 8 | 42 gm | 60 gm TEA-DBS +4 gm ODA | " | 122 gm |

*Comparison tests

Test No. 2 shows that when a 1:1-mixture of DMF and NMP is used as the solvent, the addition of IPA-DBS as an emulsifier increases the required amount of solvent in comparison to the use of no emulsifier at all. On the other hand, test No. 3 and 4 demonstrate that when DIPA-DBS or TEA-DBS is used as the emulsifier, the required amount of solvent is significantly reduced. Similarly, in the case of DMF as the solvent, tests No. 7 and 8 demonstrate that the use of DIPA-DBS or TEA-DBS as the emulsifier significantly reduces the required amount of solvent in comparison to the use of no emulsifier at all or the use IPA-DBS as the emulsifier.

The following examples illustrate the improved stability of liquid, triforine-containing concentrates comprising a member of the particular group of salts of alkylbenzenesulfonic acids as an emulsifier as against analogous concentrates comprising a different type of alkylbenzenesulfonic acid salt as an emulsifier.

EXAMPLE 2

Liquid, triforine-containing concentrates consisting of 210 gm of triforine, 20 gm of isooctadecyl alcohol and 300 gm of various amine salts of n-dodecylbenzenesulfonic acid per liter was prepared. The solvent was a 1:1 (by volume) mixture of dimethylformamide and N-methylpyrrolidone. The concentrates were then stored at 23° C. for a period of one year. After five months of storage, and again at the end of one year of storage, the relative triforine degradation in the concentrates was analytically determined. The following results were obtained:

| Emulsifier | Triforine degradation (relative) | |
|---|---|---|
| | 5 months/23° C. | 1 year/23° C. |
| IPA-DBS | 7.0% | 8.2% |
| TEA-DBS | 1.2% | 2.1% |
| DIPA-DBS | 0.8% | 1.3% |

EXAMPLE 3

Liquid, triforine-containing concentrates consisting of 160 gm of triforine, 20 gm of isooctadecyl alcohol and 240 gm of various amine salts of n-dodecylbenzenesulfonic acid per liter were prepared. The solvent was dimethylformamide. The concentrates were then stored at 23° C. for a period of eleven months. After six months of storage, and again at the end of eleven months of storage, the relative triforine degradation in the concentrates was analytically determined. The following results were obtained:

| Emulsifier | Triforine degradation (relative) | |
| --- | --- | --- |
| | 6 months/23° C. | 11 months/23° C. |
| IPA-DES | 7.0% | 8.3% |
| TEA-DES | 1.4% | 1.8% |
| DIPA-DBS | 1.2% | 1.5% |

The liquid, water-miscible, triforine-containing concentrates according to the present invention exhibit very low toxicity toward warm-blooded animals and good plant compatibility. After dilution with water to the desired concentration between 0.00001 and 0.5 percent by weight, they are effective sprays for the prophylactic as well as curative treatment of plants of all types against aphid and phytopathogenic fungi infestations. For ultra-low-volume (ULV) application the concentrates can also be dispensed in diluted form.

The liquid concentrates pursuant to the present invention are also useful for soaking seeds, such as wheat, to prevent fungus infections.

The following examples illustrate a few liquid, water-miscible, triforine-containing emulsion concentrates embodying the alkylbenzenesulfonic acid salt emulsifiers pursuant to the present invention. In each case the components are uniformly admixed with each other and, prior to use, the resulting water-miscible concentrate is diluted with water to the desired active ingredient between 0.00001 ) and 0.5 percent by weight, and the resulting aqueous emulsion is an effective fungicidal spray for agricultural and horticultural use.

EXAMPLE 4

| | 10 gm | of | triforine |
| --- | --- | --- | --- |
| | 15 gm | of | triethylamine salt of DBS |
| | 3 gm | of | isotridecyl alcohol |
| | 73 gm | of | DMF |
| Total | 101 gm | = | 100 ml of water-miscible concentrate |

EXAMPLE 5

| | 15 gm | of | triforine |
| --- | --- | --- | --- |
| | 20 gm | of | diisopropylamine salt of DBS |
| | 2 gm | of | isooctadecyl alcohol |
| | 65 gm | of | DMF |
| Total | 102 gm | = | 100 ml of water-miscible concentrate |

EXAMPLE 6

| | 15 gm | of | triforine |
| --- | --- | --- | --- |
| | 15 gm | of | triethylamine salt of DBS |
| | 2 gm | of | isohexadecyl alcohol |
| | 3 gm | of | nonylphenol condensed with 14 mols of ethyleneoxide |
| | 66 gm | of | DMF |
| Total | 101 gm | = | 100 ml of water-miscible concetrate |

EXAMPLE 7

| | 20 gm | of | triforine |
| --- | --- | --- | --- |
| | 30 gm | of | diisopropylamine salt of DBS |
| | 29 gm | of | DMF |
| | 29 gm | of | NMP |
| Total | 108 gm | = | 100 ml of water-miscible concentrate |

EXAMPLE 8

| | 20 gm | of | triforine |
| --- | --- | --- | --- |
| | 30 gm | of | triethylamine salt of DBS |
| | 2 gm | of | isooctadecyl alcohol |
| | 28 gm | of | DMF |
| | 28 gm | of | NMP |
| Total | 108 gm | = | 100 ml of water-miscible concentrate |

EXAMPLE 9

| | 20 gm | of | triforine |
| --- | --- | --- | --- |
| | 30 gm | of | triethylamine salt of DBS |
| | 2 gm | of | isooctadecyl alcohol |
| | 1 gm | of | alkyl-Modified polyvinylpyrrolidone |
| | 23 gm | of | DMF |
| | 27 gm | of | NMP |
| Total | 108 gm | = | 100 ml of water-miscible concentrate |

EXAMPLE 10

| | 22 gm | of | triforine |
| --- | --- | --- | --- |
| | 20 gm | of | lithium salt of DBS |
| | 32 gm | of | DMF |
| | 32 gm | of | NMP |
| Total | 106 gm | = | 100 ml of water-miscible concentrate |

EXAMPLE 11

| | 20 gm | of | triforine |
| --- | --- | --- | --- |
| | 30 gm | of | triethylamine salt of DBS |
| | 2 gm | of | isooctadecyl alcohol |
| | 2 gm | of | a 50% isopropanolic solution of a copolymerisate of vinylpyrrolidone and vinylacetate (1:1) |
| | 27 gm | of | DMF |
| | 27 gm | of | NMP |
| Total | 108 gm | = | 100 ml of water-miscible concentrate |

The isooctadecyl alcohol mentioned in Examples 5, 8, 9 and 11 is actually a mixture of strongly branched alcohols; the main component is 2,2,4,8,10,10-hexamethyl-5-hydroxymethyl undecane.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A liquid, water-miscible fungicidal and acaricidal composition consisting essentially of an inert solvent medium, from about 3 to about 30% by weight, based on the total weight, of N,N'-bis-(1-formamido-2,2,2-trichloroethyl)-piperazine, and from 5 to 45% by weight, based on the total weight, of an alkylbenzenesulfonic acid salt whose cation is $Ca^{++}$, $Li^+$, tert. $C_4H_9-NH_3^+$ or an ammonium ion which is derived from dimethylamine, diethylamine, di-n-propylamine, diisopropylamine, di-sec.butylamine, trimethylamine, triethylamine, tri-n-propylamine, triisopropylamine or tert.butylamine.

2. A liquid, water-miscible concentrate of claim 1, where said alkylbenzenesulfonic acid is n-dodecylbenzenesulfonic acid or tetrapropylenebenzenesulfonic acid.

3. A liquid, water-miscible concentrate of claim 1, which additionally contains from 0.5 to 10% by weight, based on the total weight, of a non-ionic emulsifier, provided, however, that the total amount of emulsifiers in said composition does not exceed 45% by weight, based on the total weight.

4. A liquid, water-miscible concentrate of claim 1, where said emulsifier is the diisopropylamine salt or the triethylamine salt of n-dodecylbenzenesulfonic acid.

5. A liquid, water-miscible concentrate of claim 1, where said solvent medium is dimethylformamide, N-methylpyrrolidone, dimethylacetamide or a mixture of any two or more of these.

6. A liquid, water-miscible concentrate of claim 1, which additionally contains a strongly branched alkanol of 12 to 20 carbon atoms as a foam depressor.

7. A liquid, water-miscible concentrates of claim 6, where said alkanol is isooctadecyl alcohol.

* * * * *

UNITED STATES PATENT AND TRADEMARK OFFICE
CERTIFICATE OF CORRECTION

PATENT NO. : 4,198,410
DATED : April 15, 1980
INVENTOR(S) : WALTER OST ET AL.

It is certified that error appears in the above-identified patent and that said Letters Patent are hereby corrected as shown below:

Column 4, line 18: "test" should read -- tests --.

Column 5, line 29: After "0.00001" the closing parenthesis ")" should be canceled.

Column 6, Example 9: "23 gm of DMF" should read -- 28 gm of DMF --.

Column 6, Example 9: "alkyl-Modified" should read -- alkyl-modified --.

Column 8, Claim 7: "A liquid, water-miscible concentrates" should read -- A liquid, water-miscible concentrate --.

Signed and Sealed this

Twenty-eighth Day of October 1980

[SEAL]

Attest:

SIDNEY A. DIAMOND

Attesting Officer

Commissioner of Patents and Trademarks